United States Patent [19]

Lowry et al.

[11] Patent Number: Plant 6,195

[45] Date of Patent: Jun. 7, 1988

[54] FLOWERING DOGWOOD—PINK PRINCESS VARIETY

[76] Inventors: John C. Lowry, 15601 Manor Rd., Monkton, Md. 21111; Matthew J. Wingle, 3rd, R.D. 1, Box 108, Augusta, N.J. 07822

[21] Appl. No.: 817,615

[22] Filed: Jan. 10, 1986

[51] Int. Cl.[4] ..... A01H 5/00
[52] U.S. Cl. ..... Plt./51
[58] Field of Search ..... Plt./51

[56] References Cited

U.S. PATENT DOCUMENTS

P.P. 4,300 9/1978 Wills ..... Plt. 51

*Primary Examiner*—James R. Feyrer
*Attorney, Agent, or Firm*—Burns, Doane, Swecker & Mathis

[57] ABSTRACT

A new and distinct variety of pink Flowering Dogwood, botanically known as *Cornus florida rubra* is provided. The new variety possesses the unique combination of the formation of attractive pink bracts and the formation of attractive variegated leaves wherein the central portion is medium green and the margin is white when mature.

2 Drawing Sheets

SUMMARY OF THE INVENTION

The new and distinct variety of pink Flowering Dogwood tree was discovered by us during the Spring of 1980 while growing among trees at the location of the Perkins DeWilde Nursery at Shiloh, N.J. The parentage and origin of the tree is unknown and it is assumed to be the result of a sport or mutation of unknown causation in *Cornus florida rubra*.

We were attracted to a single tree of the new variety because of the distinctive attractive coloration of its bracts and leaves. Upon careful observation no other tree growing in the area was found to possess the same combination of bract coloration and leaf coloration. Such distinctive colorations in combination are believed to differ from those of all previously known Flowering Dogwood varieties.

Heretofore, pink Flowering Dogwood trees have been highly prized by horticulturists because of their distinctive pink to red bracts in the springtime. Cherokee Chief (U.S. Plant Pat. No. 1,710) is an example of such a Dogwood tree. Such previously known pink Flowering Dogwood trees with the exception of the Wills cultivar (U.S. Plant Pat. No. 4,300) to the best of our knowledge have always possessed the usual green non-variegated leaves commonly encounted on Flowering Dogwood trees.

The new variety of the present invention can be readily distinguished from the Wills cultivar. For instance, the leaves of the new variety tend to be typical in size to those of the species while the leaves of the Wills cultivar tend to be smaller, the leaf margins of the new variety are considerably less wrinkled than those of the Wills cultivar, the substantially white leaf margins of the new variety tend to be substantially wider than those of the Wills cultivar, and the new variety commonly forms leaves having a more vivid Fall coloration than the Wills cultivar.

White flowering *Cornus florida* trees which possess various types of unusual variegated leaves also have been known. Representative examples of white Flowering Dogwood varieties having variegated leaves are Rainbow (U.S. Plant Pat. No. 2,743), Welchii (non-patented and sometimes known as Tricolor since pink coloration commonly is included with the white and green portions of the leaves), First Lady (U.S. Plant Pat. No. 2,916), and Holman Gold (non-patented). However, in each of these varieties, with the possible exception of Welchii, the leaf margins tend to be golden or yellow instead of white.

As a result of our continuing studies we have determined that the new variety of Flowering Dogwood possesses the following combination of characteristics:

(a) an upright growth habit,
(b) the formation of attractive pink bracts,
(c) the formation of attractive variegated leaves having a medium green central portion and a substantially white margin when mature,
(d) the formation of leaves which generally are larger than those of the Wills cultivar,
(e) the formation of leaves having leaf margins which are considerably less wrinkled than those of the Wills cultivar,
(f) the formation of leaves having substantially white margins which tend to be substantially wider than those of the Wills cultivar, and
(g) the formation of leaves which generally have a more vivid Fall coloration than the Wills cultivar.

Asexual propagation by grafting at Monkton, Md., and at Augusta, N.J., over a period of three years has confirmed that the distinctive appearance of the new variety is established and is transmitted through succeeding propagations.

The new and distinctive variety of Flowering Dogwood tree has been named the Pink Princess variety.

BRIEF DESCRIPTION OF THE PHOTOGRAPHS

The photographs show typical specimens of the new variety depicted in color as nearly true as it is reasonably possible to make the same in color illustrations of this character.

DETAILED DESCRIPTION OF NEW VARIETY

Figure 1:
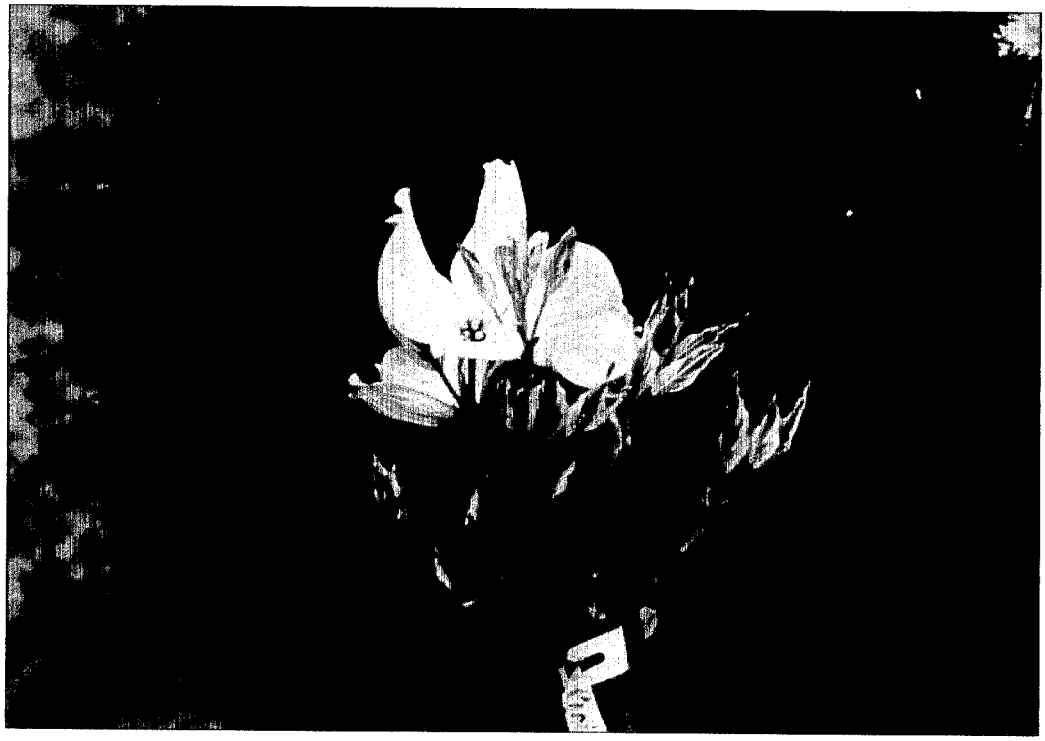
FIG. 1 illustrates the attractive pink bracts soon after opening during the first week of May, 1985, at Augusta, N.J.
Figure 2:
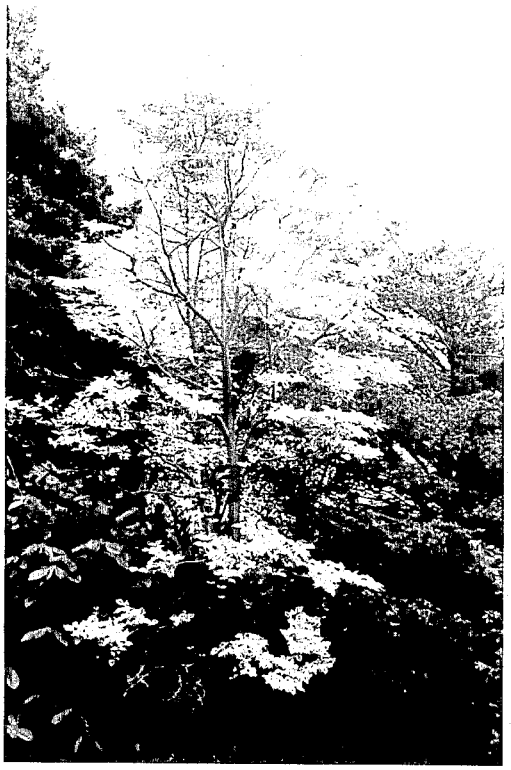
FIG. 2 illustrates the original tree of the new variety on May 16, 1985, while growing at Shiloh, N.J. At this time the pink bracts no longer are visible and the leaf margins have assumed a substantially white coloration.
Figure 3:
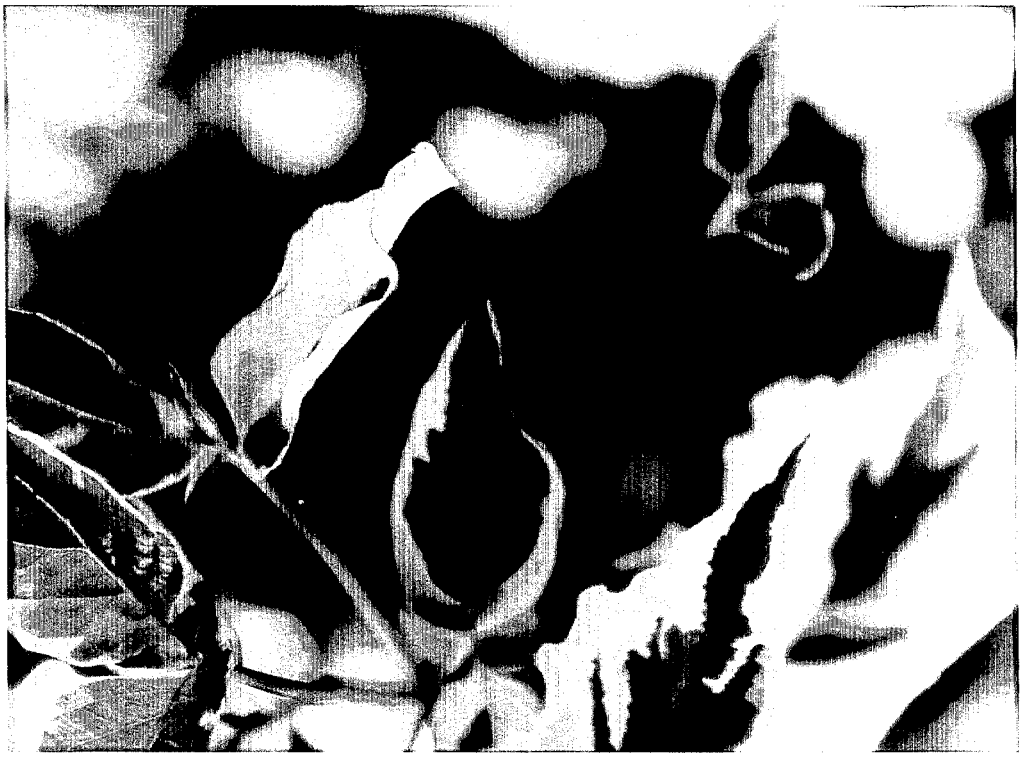
FIG. 3 illustrates representative immature leaves and more mature leaves of the new variety obtained at Augusta, N.J., during the springtime of 1985. It will be noted that the immature leaves possess a pink coloration on the margins and the mature leaves possess substantially white margins.
Figure 4:
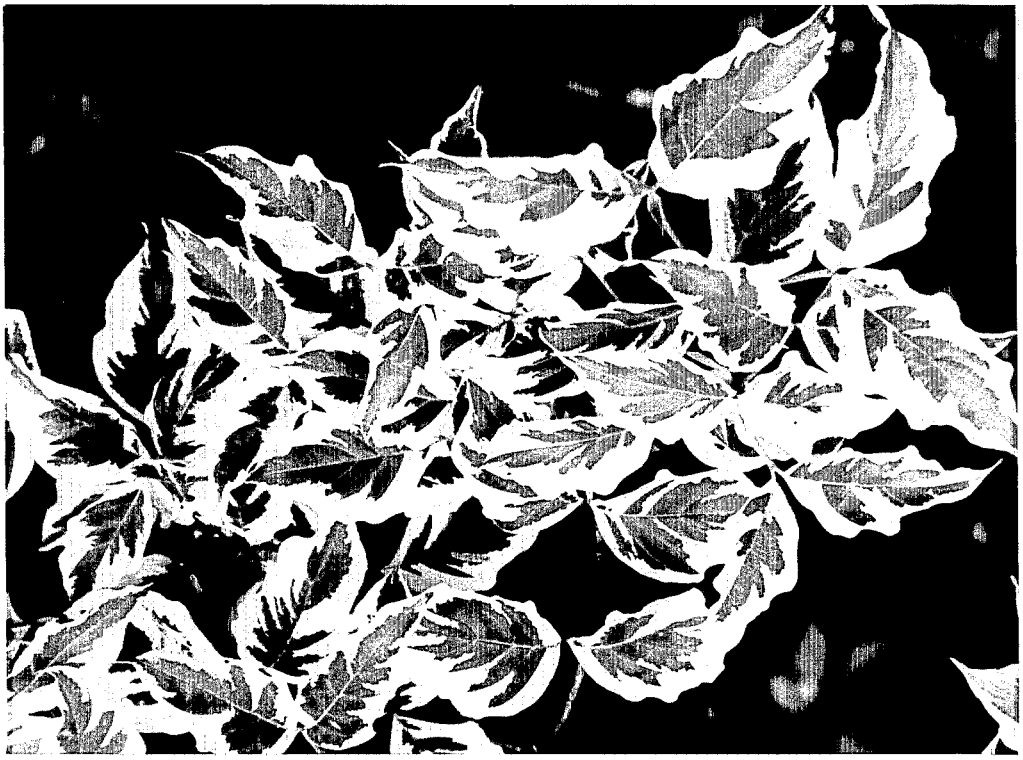
FIG. 4 illustrates representative mature leaves of the new variety obtained at Augusta, N.J., as they appeared later in the 1985 growing season. It will be noted that the leaf margins are substantially white and that the pink coloration is largely absent.

The following description was made of plants growing at Augusta, N.J. Color terminology is to be accorded its ordinary dictionary significance. Unless otherwise indicated the new variety exhibits characteristics substantially identical to those of other *Cornus florida* varieties.

Growth habit: Generally upright as illustrated.

Blossoms: The bracts of the new variety commonly open during late April or early May. Such bracts exhibit an attractive pink coloration as illustrated which tends to fade with the passage of time particularly when exposed to intense sunlight. The veins present in the bracts often are of a darker coloration than the remainder. With reference to the *R.H.S. Colour Chart* the bracts upon initial opening commonly exhibit an overall delicate pink coloration ranging from Red Group 50C to Red Group 50D with the veins present therein being of an even darker red coloration. The distance across the fully opened bracts commonly measures approximately 3½ to 4 inches.

Foliage: The central portion of the leaves is medium green in coloration which generally abruptly changes in an irregular pattern to substantially white on the margins. When immature the leaf margins initially commonly exhibits pink coloration as illustrated. The width of the leaf margins has been observed to be somewhat greater than on leaves of the Welchii variety. With reference to the *R.H.S. Colour Chart* the central portion of the mature leaves commonly approximates that of Yellow-Green Group 146A to 146C. Typical leaves commonly measure approximately 2½ to 4 inches in length and from approximately 1½ to 2¼ inches in width at the broadest point.

Disease resistance: Average.

Hardiness: Average.

We claim:

1. A new and distinct variety of pink Flowering Dogwood tree, botanically known as *Cornus florida rubra*, substantially as illustrated and described, characterized particularly as to novelty by the unique combination of:

(a) an upright growth habit, (b) the formation of attractive pink bracts, (c) the formation of attractive variegated leaves having a medium green central portion and a substantially white margin when mature, (d) the formation of leaves which generally are larger than those of the Wills cultivar, (e) the formation of leaves having leaf margins which are considerably less wrinkled than those of the Wills cultivar, (f) the formation leaves having substantially white margins which tend to be substantially wider than those of the Wills cultivar, and (g) the formation of leaves which generally have a more vivid Fall coloration than the Wills cultivar.

* * * * *